US006900054B2

(12) United States Patent
Rao et al.

(10) Patent No.: US 6,900,054 B2
(45) Date of Patent: May 31, 2005

(54) LINEAGE RESTRICTED GLIAL PRECURSORS FROM THE CENTRAL NERVOUS SYSTEM

(75) Inventors: Mahendra S. Rao, Salt Lake City, UT (US); Mark Noble, Brighton, NY (US); Margot Mayer-Proschel, Pittsford, NY (US)

(73) Assignee: University of Utah Research Foundation, Salt Lake City, UT (US)

( * ) Notice: Subject to any disclaimer, the term of this patent is extended or adjusted under 35 U.S.C. 154(b) by 57 days.

(21) Appl. No.: 09/736,728

(22) Filed: Dec. 14, 2000

(65) Prior Publication Data

US 2001/0029045 A1 Oct. 11, 2001

Related U.S. Application Data

(63) Continuation of application No. 08/980,850, filed on Nov. 29, 1997, now Pat. No. 6,235,527.

(51) Int. Cl.$^7$ .............................. C12N 5/00; C12N 5/02
(52) U.S. Cl. ..................... 435/377; 435/375; 435/368
(58) Field of Search ................................ 435/375, 377, 435/368

(56) References Cited

U.S. PATENT DOCUMENTS 5,688,692 A * 11/1997 Jat et al. ..................... 435/354
5,753,506 A *  5/1998 Johe et al. ................... 435/377

OTHER PUBLICATIONS

Gord et al. Developmental Biol. 167: 596–608, 1995.*
J. Price, et al.; The Generation of Cellular Diversity in the Cerebral Cortex, 2 Brain Pathology 23–29 (1992).
R. McKinnon, et al.; FGF Modulates the PDGF–Driven Pathway of Oligodenrocyte Development; 5 Neuron 603–614 (1990).
M. Raff, et al.; Two Types of Astrocytes in Cultures of Developing Rat White Matter: Differences in Morphology, Surface Gangliosides, and Growth Characteristics; 3 The Journal of Neuroscience 1289–1300 (1983).
R.K. Small, et al.; Evidence for migration of oligodendrocyte–type-2 astrocyte progenitor cells into the developing rat optic nerve; 328 Nature 155–157 (1987).
O. Bögler, et al.; Cooperation between two growth factors promotes extended self–renewal and inhibits differentiation of oligodendrocyte–type–2 astrocyte (O–2A) progenitor cells; 87 Proc. Natl. Acad. Sci, USA 6368–6372 (1990).
J. Sanes; Analysing cell lineage with a recombinant retrovirus; 12 TINS 21–28 (1989).
A.K. Groves, et al.; Repair of demyelinated lesions by transplantation of purified O–2Aprogenitor cells; 362 Nature 453–455 (1993).
J. E. Goldman; Lineage, migration, and fate determination of postnatal subventricular zone cells in the mammalian CNS; 24 Journal of Neuro–Oncology 61–64 (1995).

O. Bögler, et al.; Measurement of Time in Oligodendrocyte–Type–2 Astrocyte (O–2A) Progenitors Is a Cellular process Distinct from Differentiation or Division; 162 Developmental Biology 525–538 (1994).
J.B. Grinspan, et al.; Cerebral White Matter Contains PDGF–Responsive Precursors to O2A Cells; 10(6) The Journal of Neuroscience 1866–1873 (1990).
R. Hardy and R. Reynolds; Proliferation and differentiation potential of rat forebrain oligodendroglial progenitors both in vitro and in vivo; 111 Development 1061–1080 (1991).
M. C. Raff, et al.; A glial progenitor cell that develops in vitro into an astrocyte or an oligodendrocyte depending on culture medium; 303 Nature 390–396 (1983).
R. H. Miller, et al.; Clonal analysis of astrocyte diversity in neonatal rat spinal cord cultures; 113 Development 353–362 (1991).
M. Noble et al.; Purified astrocytes promote the in vitro division of a bipotential glial progenitor cell; 3 The EMBO Journal 2243–2247 (1984).
M. Mayer, et al.; Ciliary neurotrophic factor and leukemia inhibitory factor promote the generation, maturation and survival of oligodendrocytes in vitro; 120 Development 143–153 (1994).
M. Mayer–Proschel, et al.; Isolation of Lineage–Restricted Neuronal Precursors from Multipotent Neuroepithelial Stem Cells; 19 Neuron 773–785 (1997).
N. Ibarrola, et al.; Evidence for the Existence of at Least Two Timing Mechanisms That Contribute to Oligodendrocyte Generation in vitro; 180 Developmental Biology 1–21 (1996).
M. Noble, et al.; From Rodent Glial Precursor Cell to Human Glial Neoplasia in the Oligodendrocyte– Type–2 Astrocyte Lineage; 15 GLIA 222–230 (1995).
P.F. Bartlett, et al.; Rat Neural Anigen–2 (Ran–2): A Cell Surface Antigen on Astrocytes, Ependymal Cells, Müller Cells and Lepto–Me–Ninges Defined by a Monoclonal Antibody; 204 *Brain Research* 339–351 (1981).
M.C. Raff; Glial Cell Diversification in the Rat Optic Nerve; 243 Science 1450–1455 (1989).
R.H. Miller, et al.; The Macroglial Cells of The Rat Optic Nerve; 12 Ann. Rev. Neurosci. 517–534 (1989).
Z. Ikram, et al.; The biological clock that measures the mitotic life–span of mouse embryo fibroblats continues to function in the presence of simian virus 40 large tumor antigen; 91 *Proc. Natl. Acad. Sci. USA* 6448–6452 (1994).

* cited by examiner

*Primary Examiner*—Robert C. Hayes
(74) *Attorney, Agent, or Firm*—Licata & Tyrrell P.C.

(57) ABSTRACT

A glial precursor cell population from mammalian central nervous system has been isolated. These A2B5$^+$ E-NCAM$^-$ glial-restricted precursor (GRP) cells are capable of differentiating into oligodendrocytes, A2B5$^+$ process-bearing astrocytes, and A2B5$^-$ fibroblast-like astrocytes, but not into neurons. GRP cells can be maintained by regeneration in culture. GRP cells differ from oligodendrocyte-type-2 astrocyte (O-2A) progenitor cells in growth factor requirements, morphology, and progeny. Methods of use of GRP cells are also disclosed.

5 Claims, No Drawings

LINEAGE RESTRICTED GLIAL PRECURSORS FROM THE CENTRAL NERVOUS SYSTEM

This application is a continuation of prior application Ser. No. 08/980,850, filed Nov. 29, 1997, now U.S. Pat. No. 6,235,527.

BACKGROUND OF THE INVENTION

This invention relates to lineage restricted glial precursors from the central nervous system (CNS). More particularly, the invention relates to a purified population of glial restricted precursor (GRP) cells capable of differentiating into oligodendrocytes and two types of astrocytes and methods of making and using thereof.

Relatively little is known about the origins of glial cells, which represent 90% of the cells in the central nervous system (CNS). Studies on late embryonic and postnatal rats have identified (1) cells apparently restricted to differentiation into astrocytes and (2) oligodendrocyte-type-2 astrocyte (O-2A) progenitor cells able to generate oligodendrocytes and type-2 astrocytes. M. C. Raff et al., A Glial Progenitor Cell That Develops In Vitro into an Astrocyte or an Oligodendrocyte Depending on the Culture Medium, 303 Nature 390–96 (1983); M. C. Raff, Glial Cell Diversification in the Rat Optic Nerve, 243 Science 1450–55 (1989); R. K. Small et al., Evidence for Migration of Oligodendrocyte-type-2 Astrocyte Progenitor Cells into the Developing Rat Optic Nerve, 328 Nature 155–57 (1987); R. H. Miller et al., The Macroglial Cells of the Rat Optic Nerve, 12 Ann. Rev. Neurosci. 517–34 (1989); M. Noble et al., From Rodent Glial Precursor Cell to Human Glia Neoplasia in the Oligodendrocyte-type-2 Astrocyte Lineage, 15 Glia 222–30 (1995). In vivo labeling of dividing precursor cells with retroviruses has also indicated the existence of precursor cells that only generate astrocytes, and others that generate oligodendrocytes and astrocytes, J. Price et al., The Generation of Cellular Diversity in the Cerebral Cortex, 2 Brain Pathol. 23–29 (1992); J. E. Goldman, Lineage, Migration, and Fate Determination of Postnatal Subventricular Zone Cells in the Mammalian CNS, 24 J. Neurooncol. 61–64 (1995); J. R. Sanes, Analysing Cell Lineages with a Recombinant Retrovirus, 12 TINS 21–28 (1989), but the relationship of these cells to those characterized by in vitro experimentation is not yet known. How many classes of glial precursor cells there are and their developmental relationship to each other remain to be defined.

A critical missing component in understanding the development and generation of the glial cells of the central nervous system is to determine whether there exists any cell in vivo that is able to generate all three of the best-described glial populations, i.e. oligodendrocytes and cells with the characteristics of type-1 and type-2 astrocytes. Prior to the discoveries disclosed in the present patent application, the existence of such a cell was strictly hypothetical.

The ability to isolate and grow mammalian glial restricted precursor cells would allow for using pure populations of such cells for therapeutic transplantation, discovery of genes specific to selected stages of development, generation of cell-specific antibodies for therapeutic and diagnostic uses such as for targeted gene therapy, and the like. GRP's are important for transplantation therapy because of the ability of glial cells to migrate extensively after transplantation. Thus, a single injection can allow diffuse migration of cells to otherwise inaccessible sites. For example, multiple sclerosis is a disorder where oligodendrocytes and myelin sheaths are damaged. For example, transplantation of genetically modified GRPs for treating diseases of the CNS would allow cells to incorporate within the CNS parenchyma instead of forming an isolated mass of cells that provides a very high local concentration of biologically active factor(s) as a single large point source. As another example, in diseases where remyelination is required, the migration of GRP cells and/or their derivatives away from a lesion site might allow a reduced number of injections to be made in the CNS, thus simplifying surgical procedures. Dividing GRP's can also be made to express a variety of genes and can be used to deliver drugs that would not normally cross the blood-brain barrier. Exemplary of disorders that could be treated in this manner are glycogen storage disorders such as Gaucher's disease and Niemann-Pick disease. GRP's can also be used as a source for purification of trophic molecules, i.e. molecules that are selectively enriched in such cells. Further, GRP's can be used as a source of mRNA for generation of cDNA libraries that are specific for the stage of development that GRP's represent. Moreover, GRP's would provide a ready source of cells for high throughput screening of drugs.

In view of the foregoing, it will be appreciated that providing a population of tripotential glial precursor cells capable of differentiating into oligodendrocytes and two types of astrocytes, and methods of making and using thereof would be significant advancements in the art.

BRIEF SUMMARY OF THE INVENTION

It is an object of the present invention to provide isolated (pure) populations of mammalian glial restricted precursor cells.

It is also an object of the invention to provide a method of isolating a pure population of mammalian glial restricted precursor cells from the central nervous system.

It is another object of the invention to provide mammalian CNS glial cells via generation and differentiation from multipotent GRP cells isolated from mammalian central nervous system.

It is still another object of the invention to provide a purified population of mammalian glial restricted precursor cells, wherein such cells are distinct from previously described cells including (1) neuroepithelial stem (NEP) cells, (2) neural crest stem cells, (1) neurospheres, (4) E-NCAM$^+$ neuronal progenitor cells, and (5) O-2A progenitor cells.

These and other objects can be addressed by providing an isolated, pure population of mammalian CNS glial restricted precursor cells that is capable of generating oligodendrocytes and at least two distinct populations of astrocytes. These glial restricted precursor cells are preferably isolated from a mammal selected from the group consisting of human and non-human primates, equines, canines, felines, bovines, porcines, ovines, and lagomorphs. The glial restricted precursor cells express cell surface antigens recognized by the A2B5 monoclonal antibody, but do not express embryonic neural cell adhesion molecule (E-NCAM), i.e. the cells are E-NCAM$^-$. The glial restricted precursor cells are capable of self renewal in adherent feeder-cell-independent culture medium and of differentiating into CNS glial cells, including oligodendrocytes, A2B5-immunoreactive process-bearing astrocytes, and A2B5-non-immunoreactive fibroblast-like astrocytes, but not into CNS neuronal cells.

A method of isolating a pure population of mammalian CNS glial precursor cells comprises the steps of:

(a) removing a sample of CNS tissue from a mammal at a stage of development after closure of the neural tube;

(b) dissociating cells comprising the sample of CNS tissue removed from the mammal; and (c) purifying from the dissociated cells a subpopulation expressing a selected antigen defining glial restricted precursor cells.

The purified subpopulation of cells can then be grown in feeder-cell-independent culture on a substratum and in a medium configured for supporting adherent growth of the glial restricted precursor cells and at a temperature and in an atmosphere conducive to growth of the glial restricted precursor cells. In a preferred embodiment of this method, the selected antigen defining glial restricted precursor cells is a ganglioside recognized by the A2B5 antibody. The glial restricted precursor cells can be purified through procedures well known in the art, such as specific antibody capture, fluorescence activated cell sorting, magnetic bead capture, and the like.

A method of obtaining glial cells comprises:

(a) providing glial restricted precursor cells; and (b) plating the glial restricted precursor cells under differentiating conditions, thereby causing the glial restricted precursor cells to differentiate into glial cells. Non-process bearing A2B5$^-$GFAP$^+$ astrocytes are obtained by adding to the medium an effective amount of a factor that promotes differentiation into such astrocytes, e.g. fetal calf serum. Process-bearing A2B5$^+$GFAP$^+$ astrocytes are obtained by adding to the medium an effective amount of a factor that promotes differentiation into such astrocytes, e.g. ciliary neurotrophic factor and basic fibroblast growth factor. Oligodendrocytes are obtained by adding to the growth medium an effective amount of a factor that promotes differentiation into oligodendrocytes, e.g. platelet-derived growth factor and thyroid hormone (T3).

A method for treating a neurological or neurodegenerative disease comprises administering to a mammal in need of such treatment an effective amount of glial restricted precursor cells or derivatives thereof. The GRP cells can be caused to (1) proliferate and differentiate in vitro prior to being administered, or (2) proliferate in vitro prior to being administered and to further proliferate and differentiate in vivo after being administered, or (3) proliferate in vitro prior to being administered and then to differentiate in vivo without further proliferation after being administered, or (4) proliferate and differentiate in vivo after being injected directly after being freshly isolated. The GRP cells or derivatives thereof can be from a heterologous donor or an autologous donor. The donor can be a fetus, a juvenile, or an adult. The disease to be treated is preferably multiple sclerosis, spinal cord injury, CNS trauma, conditions in which axonal regeneration are desired, conditions in which control or reduction in glial scarring are desired, any dysmyelinating disorder, or an enzymatic disorder. The GRP cells or derivatives thereof can be administered locally or widely in the CNS.

A method for treating neurodegenerative symptoms in a mammal comprises the steps of:

(a) providing a pure population of glial restricted precursor cells;

(b) genetically transforming the glial restricted precursor cells with a gene encoding a growth factor, neurotransmitter, neurotransmitter synthesizing enzyme, neuropeptide, neuropeptide synthesizing enzyme, or substance that provides protection against free-radical mediated damage, thereby resulting in a transformed population of glial restricted precursor cells that express said growth factor, neurotransmitter, neurotransmitter synthesizing enzyme, neuropeptide, neuropeptide synthesizing enzyme, or substance that provides protection against free-radical mediated damage; and (c) administering an effective amount of the transformed population of glial restricted precursor cells to the mammal.

Such glial restricted precursor cells can be administered as freely diffusible cells, in an encapsulation device, or on or in a scaffold.

Another method for treating neurodegenerative symptoms in a mammal comprises the steps of:

(a) providing a pure population of glial restricted precursor cells or derivatives thereof of mixtures thereof;

(b) administering an effective amount of the population of glial restricted precursor cells or derivatives thereof or mixtures thereof to the CNS of the mammal.

Still another method for treating neurodegenerative symptoms in a mammal comprises the steps of (a) providing a pure population of glial restricted precursor cells or derivatives thereof or mixtures thereof;

(b) placing the glial restricted precursor cells or derivatives thereof or mixtures thereof in an encapsulation device to result in encapsulated cells; and (c) administering an effective amount of the encapsulated cells to the mammal.

Yet another method for treating neurodegenerative symptoms in a mammal comprises the steps of:

(a) providing a pure population of glial restricted precursor cells or derivatives thereof or mixtures thereof;

(b) placing the glial restricted precursor cells or derivatives thereof or mixtures thereof on or in a scaffold to result in scaffold-associated cells; and (c) administering an effective amount of the population of scaffold-associated cells to the mammal.

A method of using glial restricted precursor cells for reducing glial scar formation associated with surgical procedures at a lesion site in the central nervous system comprises the steps of:

(a) providing a purified population of glial restricted precursor cells or derivatives thereof or a mixture thereof;

(b) administering said an effective amount of said purified population into and adjacent to said lesion site within two weeks following traumatic injury thereto.

DETAILED DESCRIPTION

Before the present population of glial precursor cells and methods of making and using thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an embryo" includes references to two or more embryos, reference to "a mitogen" includes reference to a mixture of two or more mitogens, and reference to "a factor" includes reference to a mixture of two or more factors.

In describing and claiming the present invention, the following terminology will be used in accordance with the definitions set out below.

As used herein, "self renewal" refers to the capability of a cell to divide to produce two daughter cells, at least one of which has the same morphology, antigenic phenotype, and differentiation potential as the mother cell.

As used herein, "clonal density" and similar terms mean a density sufficiently low to result in the isolation of single, non-impinging cells when plated in a selected culture dish. An illustrative example of such a clonal density is about 225 cells/100 mm culture dish.

As used herein, "effective amount" means an amount of a growth or survival or other factor that is nontoxic but sufficient to provide the desired effect and performance. For example, an effective amount of fibroblast growth factor (FGF) as used herein means an amount selected so as to support self renewal and proliferation of GRP cells when used in combination with other essential nutrients, factors, and the like. An "effective amount" of GRP cells or derivatives thereof or mixtures thereof for transplantation refer to an amount or number of cells sufficient to obtain the selected effect. For example, an effective amount of GRP cells for treating scarring would be an amount of cells sufficient to obtain a measurable decrease in the amount of scarring. GRP cells will generally be administered at concentrations of about 5–50,000 cells/microliter. Transplantation will generally occur in volumes up to about 15 microliters per injection site. However, transplantation subsequent to surgery on the central nervous system can involve volumes many times this size. Thus, the number of cells used for transplantation is limited only by utility, and such numbers can be determined by a person skilled in the art without undue experimentation.

As used herein, "feeder—cell-independent adherent culture" or similar terms mean the growth of cells in vitro in the absence of a layer of different cells that generally are first plated on a culture dish and to which the cells from the tissue of interest are then added. In feeder cell cultures, the feeder cells provide a substratum for the attachment of cells from the tissue of interest and additionally serve as a source of mitogens and survival factors. The feeder-cell-independent adherent cultures herein use a chemically defined substratum, for example laminin, and mitogens or survival factors are provided by supplementation of the liquid culture medium with either purified factors or crude extracts from other cells or tissues. Therefore, in feeder-cell-independent cultures, the cells in the culture dish are primarily cells derived from the tissue of interest and do not contain other cell types required to support the growth of cells derived from the tissue of interest.

As used herein, a "derivative" of a GRP cell means a cell derived from a GRP cell in vitro by genetic transduction, differentiation, or similar processes.

As used herein, "administering" a GRP cell to a mammal means transplanting or implanting such GRP cell into CNS tissue or tissue adjacent to such CNS tissue of a recipient. Such administration can be carried out by any method known in the art, such as in surgery, with an infusion cannula, needle, and the like.

As used herein, "heterologous" refers to a individuals, tissues, or cells different from a transplant recipient. The transplant donor could be from the same species or a different species as the transplant recipient. For example, a heterologous donor of GRP cells for transplantation could be from a different species as the transplant recipient.

As used herein, "autologous" refers to self-generated or originating within the body. Thus, for example, an autologous donor of tissue or cells for transplantation is the same individual that receives the transplant. By way of further example, autologous cells are cells arising, transferred, or transplanted within an individual. In vitro manipulation may take place between harvesting of the cells and transplanting such cells or derivatives thereof, but is not required prior to transplantation.

As used herein, "transforming," "transducing," and similar terms mean insertion or transfer of a gene or genes into GRP cells regardless of the method of insertion or transfer. Thus, transformation can be accomplished by calcium phosphate transfection, DEAE-dextran transfection, polybrene transfection, electroporation, lipofection, infection of viruges, and the like and any other methods known in the art.

The present invention is illustrated using GRP cells isolated from the rat. The invention, however, encompasses all mammalian GRP cells and is not limited to GRP cells from the rat. Mammalian GRP cells can be isolated from human and non-human primates, equines, canines, felines, bovines, porcines, ovines, lagomorphs, and the like.

The present invention relates to a glial precursor cell population isolated from the central nervous system of a mammal. These A2B5$^+$E-NCAM$^-$ glial restricted precursor (GRP) cells can be clonally expanded and induced to differentiate in vitro into oligodendrocytes, A2B5$^+$ process-bearing astrocytes, and A2B5$^-$ fibroblast-like astrocytes, but not into neurons. Unlike previously described oligodendrocyte-type-2 astrocyte (O-2A) progenitor cells, freshly isolated GRP cells do not respond to platelet-derived growth factor (PDGF) as a mitogen or survival factor, nor do GRP cells differentiate into oligodendrocytes, or even survive, when plated on mitogen-free, chemically-defined medium. GRP cells may, however, acquire the ability to respond to PDGF as a mitogen at later stages of growth in culture. GRP cells also differ from O-2A progenitor cells (1) morphologically when grown in the presence of basic fibroblast growth factor (bFGF), and (2) in their responsiveness to conditions that induce astrocyte generation.

The basal medium used in the experiments described herein comprises DMEM-F12 (GIBCO/BRL, Gaithersburg, Md.) supplemented with 100 μg/ml transferrin (Calbiochem, San Diego, Calif.), 5 μg/ml insulin (Sigma Chemical Co., St. Louis, Mo.), 16 μg/ml putrescine (Sigma), 20 nM progesterone (Sigma), 30 nM selenious acid (Sigma), 1 mg/ml bovine serum albumin (GIBCO/BRL), plus B27 additives (GIBCO/BRL), 10 ng/ml PDGF, and 25 ng/ml basic fibroblast growth factor (bFGF). PDGF and bFGF are commercially available from multiple sources. In general, these additives were stored as 100× concentrates at −20° C. until use.

Fibronectin (New York Blood Center, New York, N.Y., or Sigma) was diluted to a concentration of 250 μg/ml in D-PBS (GIBCO/BRL). The fibronectin solution was applied to tissue culture dishes and immediately withdrawn. Laminin (GIBCO/BRL or Sigma) was subsequently applied at a concentration of 20 μg/ml, and dishes were incubated for 5 hours. Excess laminin was withdrawn, and the plates were allowed to air dry. Coated plates were then rinsed with water and allowed to dry again.

EXAMPLE 1

Differentiation of A2B5-immunoreactive Cells Into Oligodendrocytes and Two Types of Astrocytes.

A2B5$^+$ glial restricted precursor (GRP) cells were isolated directly from the central nervous systems of E13.5 rats using procedures similar to those described in M. Mayer, K. Bhakoo, M. Noble, Ciliary Neurotrophic Factor and Leukemia Inhibitory Factor Promote the Generation, Survival and Maturation of Oligodendrocytes In Vitro, 120 *Development* 143–53 (1994); M. Mayer-Proschel, A. J. Kalyani, T. Mujtaba, and M. S. Rao, Isolation of Lineage-Restricted Neuronal Precursors from Multipotent Neuroepithelial Stem Cells, 19 Neuron 773–85 (1997), hereby incorporated by reference. Briefly, Sprague Dawley rat embryos were removed at E13.5 and placed in a petri dish containing Ca/Mg-free Hanks balanced salt solution (HBSS, GIBCO/BRL). The trunk segments of the embryos were dissected using tungsten needles, rinsed, and then transferred to fresh HBSS. Trunk segments were incubated at 4° C. in 1% trypsin/EDTA solution (GIBCO/BRL). The segments were gently triturated with a Pasteur pipette to release the neural tubes from surrounding somites and connective tissue. Isolated neural tubes were transferred to a 0.05% trypsin/EDTA solution (GIBCO/BRL) for an additional period of ten minutes. Cells were dissociated by trituration and then washed and resuspended, resulting in a dissociated cell suspension.

Cells expressing E-NCAM and cells that adhered readily to tissue culture plastic were removed from the cell suspension by immunopanning with an anti-E-NCAM antibody according to the procedure of M. Mayer et al., Ciliary Neurotrophic Factor and Leukemia Inhibitory Factor Promote the Generation, Maturation, and Survival of Oligodendrocytes In Vitro, 120 Development 142–53 (1994); L. J. Wysocki & V. L. Sato, "Panning" for Lymphocytes: A Method for Cell Selection, 75 Proc. Nat'l Acad. Sci. USA 2844–48 (1978); B. A. Barres et al., Multiple Extracellular Signals Are Required for Long-term Oligodendrocyte Survival, 118 Development 283–95 (1993); M. Mayer-Proschel, A. J. Kalyani, T. Mujtaba, and M. S. Rao, Isolation of Lineage-Restricted Neuronal Precursors from Multipotent Neuroepithelial Stem Cells, 19 Neuron 773–85 (1997), hereby incorporated by reference. Briefly, the cells were enzymatically dissociated using papain or a dilute trypsin solution and the suspension was plated on an E-NCAM-antibody-coated dish to allow binding of all E-NCAM+ cells to the plate. The supernate, consisting of about 30% A2B5+ cells, was saved and then enriched to >98% purity by positive selection on immunopanning dishes coated with A2B5 antibody. These cells were scraped off and either plated at clonal density directly on fibronectin/laminin-coated grid dishes or at higher density on 12-well tissue culture plates.

These cells were observed for 5–10 days. Cultures generated oligodendrocytes, identified by expression of galactocerebroside (GalC); A2B5+ process-bearing astrocytes, identified by expression of GFAP, an astrocyte-specific cytoskeletal protein; and A2B5−GFAP+ astrocytes with fibroblast-like morphologies. No neurons were generated, as indicated by a lack of any cells expressing the neuron-specific markers β-III tubulin, E. E. Geisert & A. Frankfurter, The Neuronal Response to Injury as Visualized by Immunostaining of Class β-Tubulin in the Rat, 102 Neurosci. Lett. 127–41 (1999); M. K. Lee et al., The Expression and Posttranslational Modification of a Neuron-specific β-Tubulin Isotype During Chick Embryogenesis, 17 Cell. Motil. Cytoskel. 118–32 (1990), or neurofilament protein, J. N. Wood & B. Anderton, Monoclonal Antibodies to Mammalian Neurofilaments, 1 Biosci. Rep. 263–68 (1981), or the neuroblast marker E-NCAM, Ser. No. 08/909, 435; M. Mayer-Proschel et al., Isolation of Lineage-Restricted Neuronal Precursors from Multipotent Neuroepithelial Stem Cells, 19 Neuron 773–85 (1997). In contrast, both NEP cells and E-NCAM+ neuroblasts differentiate into neurons in these identical conditions, Ser. No. 08/852,744 and Ser. No. 08/909,435. Thus, the A2B5+ cells isolated from E13.5 CNS are glial-restricted precursor (GRP) cells.

EXAMPLE 2

Lack of Differentiation of A2B5-immunoreactive Cells Into Neurons.

The antigenic phenotypes of freshly isolated E13.5 A2B5+ cells prepared according to the procedure of Example 1 were determined according to the methods described in Ser. No. 08/852,744 and D. L. Stemple & D. J. Anderson, supra. Briefly, staining for cell surface antigens was carried out in cultures of living cells. For neurofilament proteins, such as glial fibrillary acidic protein (GFAP) and β-III tubulin, cells were fixed with acid-ethanol. Cell cultures were incubated with the selected primary antibody in blocking buffer (phosphate buffered saline (PBS), 1 mg/ml bovine serum albumin (BSA), 0.5% triton-X-100, 1% goat serum) for a period of 1 hour, rinsed with PBS, and incubated with a species-specific or class-specific secondary antibody in blocking buffer for an additional hour. Cultures were rinsed with three changes of PBS. Double-labeling and triple-labeling experiments were performed by simultaneously incubating cells in appropriate combinations of primary antibodies followed by non-cross-reactive secondary antibodies.

Sources of antibodies were as follows. Anti-GalC, B. Ranscht et al., Development of Oligodendrocytes and Schwann Cells Studied with a Monoclonal Antibody Against Galactocerebroside, 79 Proc. Nat'l Acad. Sci. USA 2709–13 (1982), A2B5 antibody, G. S. Eisenbarth et al., Monoclonal Antibody to Plasma Membrane Antigen of Neurons, 76 Proc. Nat'l Acad. Sci. USA 4913–17 (1979), and RT97 anti-neurofilament antibody, J. N. Wood & B. Anderton, Monoclonal Antibodies to Mammalian Neurofilaments, 1 Biosci, Rep. 263–68 (1981), were all grown as hybridoma supernatants and used at a dilution of 1:3. The Ran-2 monoclonal antibody, P. F. Bartlett, M. D. Noble, R. M. Pruss, M. C. Raff, S. Rattray, C. A. Williams, Rat Neuronal Antigen-2 (RAN-2): A Cell Surface Antigen on Astrocytes, Ependymal Cells, Muller Cells, and Leptomeninges Defined by a Monoclonal Antibody, 204 Brain Res. 339–51 (1981), was grown as a monoclonal supernate and used as an undiluted hybridoma-cell-conditioned medium. Monoclonal antibody against the GD3 ganglioside was obtained from Dr. Lloyd Old, Memorial Sloan Kettering Hospital, New York, N.Y. Other antibodies were obtained commercially or from depositories: antiβ-III-tubulin (GIBCO); anti-GFAP, A. Bignami et al., Localization of the Glial Fibrillary Acidic Protein in Astrocytes by Immunofluorescence, 43 Brain Res. 429–35 (1972) (Dako-Patts, Carpinteria, Calif.; 1:100); anti-E-NCAM (embryonic neural cell adhesion molecule; ATCC Developmental Studies Hybridomia Bank, Iowa City, Iowa); anti-PDGFR-α and anti-PDGFR-β, (platelet derived growth factor receptors α and β; Upstate Biotechnology, Lake Placid, N.Y.); anti-TrkA, anti-TrkB, and anti-TrkC (ZYMED Laboratories, South San Francisco, Calif.); anti-nestin, U. Lendahl et al., CNS Stem Cells Express a New Class of Intermediate Filament Protein, 60 Cell 585–95 (1990) (ATCC Developmental Studies Hybridoma Bank); and anti-thyroid hormone (T3) receptor (StressGian Biotechnology, Victoria, British Columbia, Canada). Secondary antibodies were obtained from Jackson Immunologicals (Westgrove, Pa.) or Southern Biotechnology.

The results of this experiment are shown in Table 1.

TABLE 1

| Phenotypic Marker | Percent of A2B5* Cells |
|---|---|
| Nestin | 30 |
| TrkC | 30 |
| T3 Receptor | 100 |
| GD3 | 0 |
| GFAP | 0 |
| GalC | 0 |
| PDGFRα | 0 |
| PDGFRβ | 0 |
| Ran-2 | 0 |
| E-NCAM | 0 |
| β-III tubulin | 0 |
| RT-97 | 0 |

These results show that it is possible to isolate directly from an animal a population of cells positive for labeling with the A2B5 antibody and with antibodies to the thyroid hormone receptor, a proportion of which may also express nestin and/or TrkC, but which are negative for all markers of glial differentiation (i.e. GFAP, GalC) and all markers of neuronal or neuroblast differentiation (i.e. β-III tubulin, neurofilaments, E-NCAM). Further, these cells do not express either the alpha or beta receptors for PDGF or the Ran-2 antigen, previously found to be present on type-1 astrocytes and their precursor cells, and are not labeled with the R24 anti-GD3 antibody. Thus, these cells are distinct from neuroepithelial stem cells by virtue of being A2B5-positive and by not necessarily expressing nestin. These cells are also distinct from all differentiated neural cell populations including neurons, astrocytes, and oligodendrocytes. These cells are further distinct from the previously described O-2A progenitor cells in being negative for expression of receptors for PDGF.

EXAMPLE 3
Differentiation of Individual A2B5-immunoreactive Cells Into Oligodendrocytes and Two Types of Astrocytes.

In this example, A235$^+$ GRP cells isolated from E13.5 central nervous system were immunopurified according to the procedure of Example 1, plated at clonal density in grid dishes (Nunclon), and wells containing single A2B5$^+$ cells were identified by staining after 24 hours with A2BS antibody and phycoerythrin-conjugated secondary antibody. Wells with a single positive cell were marked. At this point, >90% of the cells were viable, and all viable cells generated clones. Cells were induced to divide for 5 days in medium containing PDGF and bFGF, after which half of the clones were switched to growth in the presence of 10% fetal calf serum (FCS) to promote differentiation into astrocytes, while the other half were grown in a medium containing PDGF and thyroid hormone (T3) to promote oligodendrocyte generation. Cells were grown an additional 5 days and analyzed. Immunostaining was performed according to the procedure of Example 2.

Virtually all of the clones developing in the presence of FCS contained a mixture of A2B5$^+$GFAP$^-$ cells, A2B5$^+$ GFAP$^+$ astrocytes, and A2B5$^-$GFAP$^+$ astrocytes, with the greatest proportion of cells (>90%) being in the last category (Table 2). In contrast, clones developing in the presence of PDGF and thyroid hormone (T3) all contained GalC$^+$ oligodendrocytes and A2B5$^+$ GalC$^-$ GRP cells, but rarely contained any astrocytes. In >90% of cases, regardless of growth conditions, wells that contained viable cells after the first 24 hours of growth generated viable clones of cells. These results indicated that all clones could generate oligodendrocytes, A2B5$^+$GFAP$^+$ process-bearing astrocytes, and A2B5$^-$GFAP$^+$ fibroblast-like astrocytes. These results further demonstrated that the distinct patterns of differentiation emerging in these two growth conditions were not due to differential selection of separate precursor cell populations.

TABLE 2

| Antigen Expressed by | Differentiation Medium | |
|---|---|---|
| Cells in a Clone | FCS | PDGF/T3 |
| A2B5 and GFAP | 126 | 2 |
| A2B5 and GalC | 3 | 74 |
| GFAP only | 0 | 0 |
| GalC only | 0 | 0 |
| A2B5 only | 0 | 0 |
| Total Clones | 132[a] | 81[b] |

[a]Three clones died as single cells.
[b]Five clones died as single cells.

EXAMPLE 4
Self Renewal of A2B5-immunoreactive Cells.

In this example, to examine whether GRP cells were capable of extensive self-renewal without loss of differentiation potential, 5 primary clones were recloned in medium containing PDGF and bFGF. Immunopurified E13.5 cells prepared according to the procedure of Example 1 were grown in the presence of PDGF and bFGF for three days and then replated at clonal density on 5 grid dishes and cultured in the presence of PDGF and bFGF. After 5 days, all grid dishes were scored for the number of clones. From each grid dish, clones were randomly selected, and a single clone was sterilely dissociated by trituration with a fine Eppendorf pipette tip. This single clone was then further triturated in 1 ml of medium through a 25 ga. needle. This 1-ml. solution was then replated on 5 separate cloning dishes. From these 5 secondary dishes, one clone was randomly selected after 5 days and the process repeated to yield tertiary clones.

Dishes were then again switched to medium containing either FCS to promote differentiation into astrocytes or PDGF and T3 to promote differentiation into oligodendrocytes. In each condition, three descendant clones of each initial clone were chosen for analysis, thus yielding 15 clones grown under each condition. Immunostaining was carried out according to the procedure of Example 2. The results of these experiments are shown in Table 3.

TABLE 3

| Antigen Expressed by | Differentiation Medium | |
|---|---|---|
| Cells in a Clone | FCS | PDGF/T3 |
| A2B5 and GFAP | 15 | 0 |
| A2B5 and GalC | 0 | 15 |
| GFAP only | 0 | 0 |
| GalC only | 0 | 0 |
| A2B5 only | 0 | 0 |
| Total Clones | 15 | 15 |

These results show that tertiary clones exhibited an identical pattern of differentiation as primary clones. Thus, not only can individual WARP cells generate oligodendrocytes and two types of astrocytes, but the ability of these cells to undergo this tripotential differentiation is a stable property that is maintained through extensive propagation in vitro.

EXAMPLE 5
Phenotypic Differences of A2B5-immunoreactive Cells and O-2A Progenitor Cells.

In this example, GRP cells prepared and immunopurified according to the procedure of Example 1 were directly compared to O-2A progenitor cells, which are also glial-restricted A2B5$^+$ precursor cells that are able to generate glia but not neurons, M. C. Raff et al., supra. O-2A cells were immunopurified, according to the procedure of Example 1, from corpus callosum or optic nerve dissected from the central nervous systems of 7 day postnatal ("P7") rat pups. When GRP cells were grown in a mitogen-free chemically-defined medium, DMEM-BS, J. E. Bottenstein & G. H. Sato, Growth of a Rat Neuroblastoma Cell Line in Serum-free Supplemented Medium, 76 Proc. Nat'l Acad. Sci. USA 514–17 (1979), hereby incorporated by reference, the GRP cells died without differentiating. In contrast, O-2A progenitor cells completely differentiated into oligodendrocytes under identical conditions. M. C. Raff et al., supra; M. Noble & K. Murray, Purified Astrocytes Promote the In Vitro Division of a Bipotential Glial Progenitor Cell, 3 EMBO J. 2243–47 (1984). Freshly isolated GRP cells also died if grown in DMEM-BS supplemented with PDGF, whereas purified O-2A progenitor cells grew as dividing cultures, as had previously been observed, N. Ibarrola et al., Evidence for the Existence of At Least Two Timing Mechanisms That Contribute to Oligodendrocyte Generation In Vitro, 180 Dev. Biol. 1–21 (1996).

GRP cells and O-2A cells were also compared with respect to antigen expression. The cells were immunopurified as described above from E13.5 central nervous system and P7 corpus callosum, respectively, allowed to adhere overnight, and then stained by immunostaining. Immunostaining was carried out according to the procedure of Example 2. The results of these assays are shown in Table 4.

TABLE 4

|         | Percent of Cells |     |
|---------|------------------|-----|
| Antigen | E13.5            | P7  |
| Nestin  | 30               | 50  |
| TrkC    | 30               | 100 |
| PDGFRα  | 0                | 70  |
| PDGFRβ  | 0                | 0   |
| FGF-R3  | 0                | 0   |

Consistent with the lack of effect of PDGF on these freshly isolated cells, freshly isolated GRP cells were not labeled by antibodies to the PDGF-α or PDGF-β receptor. In contrast, freshly isolated O-2A progenitor cells were labeled by antibodies to the PDGF-α or PDGF-β receptor. The ability of GRP cells to respond to PDGF as a mitogen was acquired, however, after several days of in vitro growth in medium containing both bFGF and PDGF. In addition to initial differences in PDGF receptor expression, cells induced to divide by growth in the presence of bFGF had different morphologies, with O-2A progenitor cells growing as multipolar cells, as had previously been observed, 0. Bögler et al., Cooperation Between Two Growth Factors Promotes Extended Self-renewal and Inhibits Differentiation of Oligodendrocyte-type-2 Astrocytes (O-2A) Progenitor Cells, 87 Proc. Nat'l Acad. Sci. USA 6368–72 (1990); R. D. McKinnon, et al., FGF Modulates the PDGF-driven Pathway of Oligodendrocytic Development, 5 Neuron 603–14 (1990), and GRP cells growing as unipolar and bipolar cells. As discussed in the following example, the most essential difference between these two cellular populations is in their differentiation potential. O-2A progenitor cells are bipotential cells able to generate oligodendrocytes and type-2 astrocytes. In contrast, GRP cells are, at a minimum, tripotential cells able to make oligodendrocytes and two distinct astrocyte populations.

These results demonstrate that GRP cells and O-2A cells differ in their ability to survive in mitogen-free medium, their antigenic expression, and their morphology.

EXAMPLE 6
Differences in Differentiation Potential of A2B5Immunoreactive Cells and O-2A Progenitor Cells.

In this example, GRP cells and O-2A progenitor cells were directly compared for their capacities to differentiate into astrocytes. Immunopurified GRP cells and O-2A progenitor cells were grown in medium supplemented with either FCS or bFGF and ciliary neurotrophic factor (CNTF; Peprotech, Inc., Rocky Hill, N.J.) for 5 or 10 days and then labeled with A2B5, anti-GFAP, and anti-GalC antibodies. O-2A progenitor cells exposed to FCS differentiated into type-2 astrocytes, which are process-bearing A2B5$^+$GFAP$^+$ cells. M. C. Raff et al., 303 Nature 390–396 (1983); M. C. Raff et al., 3 J. Neurosci. 1289–1300 (1983). In contrast, GRP cells exposed to FCS differentiated predominantly (>90%) into non-process bearing GFAP$^+$ astrocytes that were A2B5$^-$. Preferential generation of process-bearing A2B5$^+$GFAP$^+$ astrocytes by GRP cells could be induced, however, by exposure of cells to CNTF and bFGF. In this condition, O-2A progenitor cell cultures consisted predominantly of progenitor cells, some oligodendrocytes (as has been observed previously, M. Mayer et al., supra), and rare type-2 astrocytes.

The two astrocyte phenotypes generated from GRP cells in either of these differentiation condition were stable in vitro, suggesting that these cells represent distinct astrocyte populations. The expression of other markers by these astrocytes was therefore examined. Table 5 shows the results of this study.

TABLE 5

| Phenotype | E13.5 | P7 |
|-----------|-------|-----|
| GFAP      | +     | +  |
| A2B5      | +     | +  |
| FGFR3     | −     | −  |
| Ran-2     | −     | −  |
| flat      |       | +  |
| stellate  | +     | +  |

A2B5$^-$ astrocytes expressed the FGFR3 isoform of the FGF receptor and were Ran-2$^+$. P. F. Bartlett et al., Rat Neuronal Antigen-2 (RAN-2): A Cell Surface Antigen on Astrocytes, Ependymal Cells, Muller Cells, and Leptomeninges Defined by a Monoclonal Antibody, 204 Brain Res. 339–51 (1981). In contrast, A2B5$^+$ astrocytes were Ran-2$^-$ and did not express FGFR3. Although the characteristics of these two populations would be consistent with their classification as type-1 and type-2 astrocytes, R. H. Miller et al., supra; M. C. Raff et al., 3 J. Neurosci. 1289–1300 (1983), it may be premature to assign these terminologies in light of observations that the spinal cord may contain as many as five distinct astrocyte populations, R. H. Miller & V. Szigeti, Clonal Analysis of Astrocyte Diversity in Neonatal Rat Spinal Cord Cultures, 113 Development 353–62 (1991).

Thus, GRP cells and O-2A progenitor cells were also seen to be different in their capacities to differentiate into astrocytes.

Therefore, GRP cells represent a novel glial precursor cell population capable of generating oligodendrocytes and two distinct astrocyte populations. Further, GRP cells differ in many regards from any previously described precursor cell able to generate glial cells of the central nervous system. In particular, no other glial precursor cell has been identified with as broad a differentiation potential. GRP cells differ extensively from O-2A progenitor cells, as shown herein. GRP cells also differ from the A2B5⁻ pre-O-2A progenitor cell that has been described in cultures of rat cortex. J. B. Grinspan et al., Cerebral White Matter Contains PDGF-responsive Precursors to O-2A Cells, 10 J. Neurosci. 1866–73 (1990); R. Hardy & R. Reynolds, Proliferation and Differentiation Potential of Rat Forebrain Oligodendroglial Progenitors Both In Vitro and In Vivo, 111 Development 1061–80 (1991). Moreover, GRP cells represent the earliest known precursor cell restricted in differentiation potential to the glial lineages. GRP cells thus may represent the complementary precursor cell to the neuron-restricted precursor (NRP) cells that have been isolated from E13.5 central nervous system, Ser. No. 08/852,744; M. Mayer-Pröschel et al., Isolation of Lineage-restricted Neuronal Precursors from Multipotent Neuroepithelial Stem Cells, 19 Neuron 773–85 (1997). GRP and NRP cells may, therefore, represent the canonical lineage-restricted blast cells of the central nervous system, analogous to the proposed early segregation of myeloid and lymphoid cells from the totipotent hematopoietic stem cell.

Transplanted cells can be administered to any animal, including humans, with abnormal neurological or neurodegenerative symptoms obtained in any manner, including as a result of chemical or electrolytic lesions, as a result of experimental destruction of neural areas, or as a result of aging processes. Transplantation can be bilateral, or, for example in patients suffering from Parkinson's Disease, can be contralateral to the most-affected side. Surgery is preferably performed such that particular brain regions are located, such as in relation to skull sutures, and surgery performed with stereotactic techniques. Alternatively, cells can be implanted in the absence of stereotactic surgery. Cells can be delivered to any affected neural areas using any method of cell injection or transplantation known in the art.

Cells injected to a particular neural region form a glial graft, which may have multiple functions. The capacity of GRP cells to generate oligodendrocytes allows these cells to be used in repair of demyelinating damage. The ability of these cells to make immature astrocytes allows the use of such cells as a source of chemotactic and cell-surface signals to promote growth of axons. Orientation of the transplanted cells within a scaffold permits oriented growth of such axons.

In another embodiment of the invention, progenitor (GRP) cells are transplanted into a host, and induced to proliferate and/or differentiate in that host by either (1) proliferate and differentiate in vitro prior to being administered, or (2) proliferate in vitro prior to being administered and to further proliferate and differentiate in vivo after being administered, or (3) proliferate in vitro prior to being administered and then to differentiate in vivo without further proliferation after being administered, or (4) proliferate and differentiate in vivo after being injected directly after being freshly isolated.

GRP cells can also be used for delivery of therapeutic or other compounds. Methods for bypassing the blood-brain barrier for purposes of delivery of therapeutic compounds include implanting cells in an encapsulation device according to methods known in the art or directly implanting genetically-engineered cells such that the cells themselves produce the therapeutic compound. Such compounds may be small molecules, peptides, proteins, or viral particles. Cells can be genetically transduced by any means known in the art, including calcium phosphate transfection, DEAE-dextran transfection, polybrene transfection, electroporation, lipofection, infection of viruses, and the like. Cells are first genetically manipulated to express a therapeutic substance and then transplanted either as free cells able to diffuse and incorporate within the CNS parenchyma or are contained within an encapsulation device. R. P. Lanza & W. L. Chick, Encapsulated Cell Therapy, Sci. Amer.: Sci. & Med., Jul./Aug., 16–25 (1995); P. M. Galletti, Bioartificial Organs, 16 Artifical Organs 55–60 (1992); A. S. Hoffman, Molecular Engineering of Biomaterials in the 1990s and Beyond: A Growing Liason of Polymers with Molecular Biology, 16 Artificial Organs 43–49 (1992); B. D. Ratner, New Ideas in Biomaterials Science—A Path to Engineered Biomaterials, 27 J. Biomed. Mal. Res. 837–50 (1993); M. J. Lysaght et al., Recent Progress in Immunoisolated Cell Therapy, J. Cell. Biochem. Vo. 56, 196–203 (1994), hereby incorporated by reference.

Transplanted cells can be identified by prior incorporation of tracer dyes such as rhodamine or fluorescein-labeled microspheres, fast blue, bis-benzamide, or genetic markers incorporated by any genetic transduction procedure known in the art to allow expression of such enzymatic markers as beta-galactosidase or alkaline phosphatase.

Any expression system known in the art can be used to express the therapeutic compound, so long as it has a promoter that is active in the cell, and appropriate internal signals for initiation, termination and polyadenylation. Examples of suitable expression vectors include recombinant vaccinia virus vectors including pSC11, or vectors derived from viruses such as Simian Virus 40, from Rous Sarcoma Virus, from mouse mammary tumor virus, from adenovirus, from herpes simplex virus, from bovine papillomavirus, from Epstein-Barr virus, from lentiviruses, or any other eukaryotic expression vector known in the art. Many of such expression vectors are commercially available.

Cells can also be transduced to express any gene coding for a neurotransmitter, neuropeptide, neurotransmitter-synthesizing enzyme or neuropeptide synthesizing enzyme for which expression in the host is desired.

GRP cells and/or their derivatives cultured in vitro can be used for the screening of potentially neurologically therapeutic compositions. These compositions can be applied to cells in culture at varying dosages, and the response of the cells monitored for various time periods. The induction of expression of new or increased levels of proteins such as enzymes, receptors and other cell surface molecules, or of neurotransmitters, amino acids, neuropeptides, and biogenic amines can be analyzed with any technique known in the art that can identify the alteration of the level of such molecules, including protein assays, enzymatic assays, receptor binding assays, enzyme-linked immunosorbent assays, electrophoretic analysis, analysis with high performance liquid chromatography, Western blots, and radioimmune assays. Nucleic acid analysis such as Northern blots can be used to examine the levels of mRNA coding for these molecules, or for the enzymes that synthesize these molecules. Alternatively, cells treated with these pharmaceutical compositions can be transplanted into an animal and their survival, ability to form oligodendrocytes or astrocytes, and to express any of the functions of these cell types can be analyzed by any procedures available in the art.

GRP cells can be cryopreserved by any method known in the art.

EXAMPLE 7
Use of GRP Cells and/or Their Derivatives for Repair of Demyelinating Lesions.

GRP cells are isolated by the methods of Example 1. Cells are obtained from human embryonic or adult CNS or from xenogeneic sources from which immunorejection of cells is not a clinical problem, such as pigs genetically engineered so as not to present a foreign stimulus to the human immune system. Cells collected from embryos are obtained by dissection of CNS tissue following routine abortion procedures and tissue collection in a sterile collection apparatus. Cells from the postnatal CNS are obtained by digestion of tissue following routine autopsy. Tissue is prepared, cells are immunopurified, and the resulting purified cells are cultured as in Example 1.

Cells can be transplanted directly or can first be expanded in vitro prior to transplantation. Populations expanded in vitro can further be expanded in conditions that enhance the generation of oligodendrocytes or cells committed to the generation of oligodendrocytes.

Transplantation of glial precursor cells for the purpose of remyelination has previously been demonstrated with O-2A progenitor cells, e.g., A. K. Groves, S. C. Barnett, R. J. M. Franklin, A. J. Crang, M. Mayer, W. F. Blakemore, and M. Noble, Repair of Demyelinated Lesions by Transplantation of Purified O-2A Progenitor Cells, 362 Nature 453–55 (1993). O-2A progenitor cells expanded for extended periods in vitro have limitations in their ability to undergo continued cell division when exposed to PDGF alone. O. Bögler, & M. Noble, Measurement of Time in Oligodendrocyte-type-2 Astrocyte (O-2A) Progenitors is a Cellular Process Distinct from Differentiation or Division. 162 Dev. Biol. 525–38 (1994). In contrast, GRP cells can be expanded extensively in vitro without showing such limitations in their subsequent behavior, indicating that GRP cells and their derivatives provide a much more potent source of cells for repair of CNS damage than O-2A progenitor cells. That extensive remyelination can be achieved with homogeneous precursor cell populations has been demonstrated with O-2A progenitor cells, in experiments that also demonstrated that genetically modified O-2A progenitor cells are also capable of carrying out the same functions in CNS repair as unmodified O-2A progenitor cells, and that cell populations can be greatly expanded in vitro by appropriate growth factors to create populations of cells suitable for transplantation and genetic manipulation without recourse to the generation of immortalized or conditionally immortalized cell lines, e.g., A. K. Groves, S. C. Barnett, R. J. M. Franklin, A. J. Crang, M. Mayer, W. F. Blakemore, and M. Noble, Repair of Demyelinated Lesions by Transplantation of Purified O-2A Progenitor Cells, 362 Nature 453–55 (1993).

Transplantation of cells is routinely carried out at cell suspensions of 5–50,000 cells/$\mu$l in physiological salt solutions. Cells can be transplanted into or near any CNS regions where myelin has been destroyed due to acute injury or chronic degenerative processes. Transplantation procedures, with appropriate modifications for use in human patients, are in their essence similar to procedures well known to those skilled in the art for transplantation of O-2A progenitor cells, e.g., A. K. Groves, S. C. Barnett, S. C., R. J. M. Franklin, A. J. Crang, M. Mayer, W. F. Blakemore, and M. Noble, Repair of Demyelinated Lesions by Transplantation of Purified O-2A Progenitor Cells, 362 Nature 453–55 (1993), hereby incorporated by reference.

More specifically, transplantation is performed using a computed tomographic sterotaxic guide. The patient is operated on using any of the procedures known in the art. In cases where precisely localized transplantation is desirable, the patient undergoes CT scanning to establish the coordinates of the region to receive the transplant. The injection cannula can be in any configuration used by those skilled in the relevant arts. The cannula then is inserted into the brain to the correct coordinates, then removed and replaced with a 19-gauge infusion cannula that has been preloaded with cell suspension in a small selected volume. The cells are then slowly infused, at rates generally of 1–10 ml per minute as the cannula is withdrawn. For some diseases in which it is desirable to spread cells over the largest possible area, multiple stereotactic needle passes may be made throughout the area. Patients are examined post-operatively for hemorrhage or edema. Neurological evaluations are performed at various post-operative intervals, as well as PET scans if these can be used to determine the metabolic activity of the implanted cells. These and similar procedures can be used for any implantation of GRP cells for any of the purposes indicated in this invention.

Success of remyelination is determined by non-invasive analysis with, for example, nuclear magnetic resonance image scanners, and/or by analysis of functional recovery according to methods well known in the art.

EXAMPLE 8
Use of Genetically Engineered GRP Cells and/or Their Derivatives for Repair of Demyelinating Lesions.

In this example, GRP cells are genetically modified ex vivo before introduction into or near regions of demyelination to express gene products that will make the transplanted cells resistant to destruction in vivo and/or to express gene products that provide trophic support to host cells and/or to express gene products that limit destructive processes occurring in the host. Genetic modification is carried out by any of the techniques known to those skilled in the arts, including but not limited to calcium phosphate transfection, DEAE-dextran transfection, polybrene transfection, electroporation, lipofection, infection of viruses, and the like. Gene products that would make cells resistant to destruction in vivo and/or to express gene products that provide trophic support to host cells and/or to express gene products that limit destructive processes occurring in the host include but are not limited to insulin-like growth factor-I, decay accelerating factor, catalase, superoxide dismutase, members of the neurotrophin family, glial-derived neurotrophic factor, ciliary neurotrophic factor, leukemia inhibitory factor, fas ligand, cytokines that inhibit inflammatory processes, receptor fragments that inhibit inflammatory processes, antibodies that inhibit inflammatory processes, and so forth.

EXAMPLE 9
Use of GRP Cells and/or Their Derivatives for Control of Scarring in the Central Nervous System.

It is clear that transplantation of glial cells from embryonic or young postnatal animals causes a reduction in the extent of glial scar formation associated with surgical procedures in the CNS, as shown in G. M. Smith et al., Changing Role of Forebrain Astrocytes During Development, Regenerative Failure, and Induced Regeneration upon Transplantation, 251 J. Comp. Neurol. 23–43 (1986); J. Houle, The Structural Integrity of Glial Scar Tissue Associated with a Chronic Spinal Cord Lesion Can Be Altered by Transplanted Fetal Spinal Cord Tissue, 31 J. Neurosci. Res. 120–30 (1992). Specifically, transplantation of astrocytes derived from CNS tissue at an embryonic or early postnatal age reduces glial scarring following the surgical manipulation of transplantation. As the GRP cells are the earliest isolated precursor of glial cells, glial cells derived from GRP cells express embryonic characteristics. Thus, in situations where scar formation in the CNS is expected (which include both COPS trauma and neurosurgical interventions), transplantation of GRP cells is carried out as in Example 7 to reduce or inhibit scar formation. Within two weeks following traumatic injury, cells are injected into and around the lesion site. Alternatively, in association with surgery in the CNS, in which gliotic scarring would be expected to occur, cells are injected into the operated area at the time of surgery, or within several days thereafter, using injection procedures similar to those described in Example 7 or as otherwise commonly known to those skilled in the art.

Transplantation can be of freely diffusing cells that incorporate within the CNS parenchyma, or can be of encapsulated cells releasing soluble factors that inhibit CNS scar formation. Encapsulated cells can be contained in any of the packaging systems generally known in the art.

The use of freely diffusing cells or of encapsulated cells will in general be at the discretion of the physician, under the general principle that free cells will be implanted in conditions where integration into the host tissue is desired and/or when autologous cells are utilized and/or when immune rejection of injected cells is not a concern. Encapsulated cells will in general be utilized in conditions in which the activity of diffusible factors derived from GRP cells and/or their derivatives is sufficient to control scar formation and/or in circumstances in which it will be desired to remove the GRP cells and/or their derivatives at a later time and/or in circumstances where it is necessary to utilize encapsulation procedures to shield the GRP cells and/or their derivatives from interactions with the host's immune system.

EXAMPLE 10

Use of GRP Cells and/or Their Derivatives in the Amelioration of Scarring in the Chronically Injured CNS.

It is clear that transplantation of embryonic CNS tissue into chronically injured CNS tissue can beneficially alter the integrity of glial scar tissue and even cause disappearance of scars. J. Houle, The Structural Integrity of Glial Scar Tissue Associated with a Chronic Spinal Cord Lesion Can Be Altered by Transplanted Fetal Spinal Cord Tissue, 31 J. Neurosci. Res. 120–30 (1992); J. D. Houle & P. J. Reier, Transplantation of Fetal Spinal Cord Tissue into the Chronically Injured Adult Rat Spinal Cord, 269 J. Comp. Neurol. 535–547 (1988).

As the GRP cell is the earliest isolated precursor of glial cells, glial cells derived from GRP cells express certain embryonic characteristics. Thus, in situations where scar formation is believed to be limiting of recovery in the CNS, for example in spinal cord injury (or other conditions in which scar tissue is thought to limit axonal regeneration) or in multiple sclerosis (or other conditions in which glial scar tissue is suspected to limit migration of cells of value in remyelination), transplantation of GRP cells is carried out as in Example 7 to ameliorate existing scars, thus allowing regeneration better to proceed. Transplantation can be of freely diffusing cells that incorporate within the CNS parenchyma, or can be of encapsulated cells releasing soluble factors that ameliorate CNS scar formation.

In situations where existing scar tissue could inhibit the effective repair by other cells transplanted to the CNS, co-injection with GRP cells and/or their derivatives can be used to enhance the regeneration promoted by the other injected cells. For example, in situations in which O-2A progenitor cells might be more effective than GRP cells and/or their derivatives in repairing demyelinating CNS damage but in which existing glial scar tissue would form a barrier to the effective movement of O-2A progenitor cells into the demyelinated regions, co-injection of O-2A progenitor cells with GRP cells can be used to enhance the remyelination capacity of the O-2A progenitor cells by ameliorating the gliotic scar tissue. In situations where neurons and/or precursor cells for neurons are injected into CNS tissue where existing scars, or scars formed as a result of the surgical injection procedure itself, could be expected to exert inhibitory effects on axonal regrowth, co-injection of GRP cells and/or their derivatives can be used to ameliorate the gliotic scar. Transplantation can be of freely diffusing cells that incorporate within the CNS parenchyma, or can be of encapsulated cells releasing soluble factors that ameliorate CNS scar formation.

EXAMPLE 11

Use of GRP Cells and/or Their Derivatives for the Promotion of Wound-healing in the CNS.

It is clear that transplantation of glial cells from embryonic or young postnatal animals promotes rapid wound healing in the CNS, inhibits extensive bleeding, and reduces necrosis, as shown in G. M. Smith et al., Changing Role of Forebrain Astrocytes During Development, Regenerative Failure, and Induced Regeneration upon Transplantation, 251 J. Comp. Neurol. 23–43 (1988).

As the GRP cell is the earliest isolated precursor of glial cells, glial cells derived from GRP cells express certain embryonic characteristics. Thus, in situations where promotion of wound healing is desired, as in trauma and neurosurgical interventions, injection of GRP cells and/or their derivatives can be used to promote such healing. Transplantation of cells is, in general, carried out similarly as described in Example 7, with cells being transplanted into the region of the brain or spinal cord in which promotion of wound healing is desired. Transplantation may be of freely diffusing cells that incorporate within the CNS parenchyma, or may be of encapsulated cells releasing soluble factors that promote wound healing.

EXAMPLE 12

Use of GRP Cells and/or Their Derivatives or Genetically Modified GRP Cells and/or Their Derivatives to Promote Neuronal Survival and/or Axonal Regeneration in the CNS.

It is known that astrocytes derived from embryos or young postnatal animals can promote extensive axonal outgrowth when transplanted to the adult CNS, G. M. Smith et al., Changing Role of Forebrain Astrocytes During Development, Regenerative Failure, and Induced Regeneration upon Transplantation, 251 J. Comp. Neurol. 23–43 (1986), and that genetically modified fibroblasts can be used to secrete trophic factors that promote survival and growth of CNS axons, e.g., R. Grill et al., Cellular Delivery of Neurotrophin-3 Promotes Corticospinal Axonal Growth and Partial Functional Recovery After Spinal Cord Injury, 17 J. Neurosci. 5560–72 (1997), and references therein; M. D. Kawaja et al., Grafting Genetically Modified Cells within the Rat Central Nervous System:: Methodological Considerations, in Neural Transplantation: A Practical Approach 21–56, (S. B. Dunnett & A. Bjorklund eds., 1992), and references therein; L. F. Fisher et al., Use of Genetically Modified Cells to Deliver Neurotrophic Factors and Neurotransmitters to the Brain, in Providing Pharmacological Access to the Brain: Alternate Approaches 329–47 (R. Flanagan, D. F. Emerich and S. R. Winn eds., 1995), and references therein.

Transplantation of GRP cells and/or their derivatives is according to Example 7, into regions of neuronal injury or regions in which axonal regeneration is required.

Genetically modified GRP cells can be used to supply factors that promote neuronal survival and/or axonal regeneration (e.g., nerve growth factor, brain-derived neurotrophic factor, neurotrophin-3, glia-derived neurotrophic factor, nurturin, L1 adhesion molecule and other factors known to those in the art) in preference to the use of genetically modified non-neural cells due to the ability of glial cells and their precursors to integrate effectively within the host parenchyma. Cells can be genetically transduced by any means known in the art, including calcium phosphate transfection, DEAE-dextran transfection, polybrene transfection, electroporation, lipofection, infection of viruses, and the like. Cells are first genetically manipulated to express a therapeutic substance and then transplanted as free cells able to diffuse and incorporate within the CNS parenchyma.

In situations in which it is desired to provide a source of trophic factors but to retain the ability to remove the transplanted cells, or when immune rejection is a potential problem, then genetically modified GRP cells and/or their derivatives can be encapsulated in any of a variety of encapsulation devices known to those skilled in the art prior to implantation.

EXAMPLE 13
Use of GRP Cells and/or Their Derivatives to Promote Axonal Regeneration in the CNS Along Defined Scaffolds.

It is known that astrocytes derived from embryos or young postnatal animals can promote extensive axonal growth when transplanted to the adult CNS, and that transplantation of such astrocytes on a scaffolding material can lead to direction of axonal growth in desired directions, G. M. Smith et al., Changing Role of Forebrain Astrocytes During Development, Regenerative Failure, and Induced Regeneration upon Transplantation, 251 J. Comp. Neurol. 23–43 (1986).

GRP cells and/or their derivatives recapitulate the properties of immature glia in promoting axonal growth in the adult CNS. These cells can be implanted in or on a variety of scaffolding materials well known to practitioners of the art, providing a surface of immature glial cells to promote axonal growth in desired directions.

GRP cells and/or their derivatives growing on cellular scaffolds are implanted in such a manner as to form a bridge between a region where a desired population of neurons exists and the region(s) to which neuronal growth is being directed. For example, in the injured spinal cord, such scaffolds, on which GRP cells and/or their derivatives are growing, are implanted so as to form a bridge between the caudal and rostral portions of the injured spinal cord.

EXAMPLE 14
Use of Genetically Modified-GRP Cells and/or Their Derivatives as Substrates for Growth of Regenerating Axons in the CNS.

In this example there is described a process for enhancing the ability of GRP cells and/or their derivatives to promote neuronal survival and axonal elongation in the CNS It is known that astrocytes derived from embryos or young postnatal animals can promote extensive axonal growth when transplanted to the adult CNS, and that transplantation of such astrocytes on a scaffolding material can lead to direction of axonal growth in desired directions. G. M. Smith et al., Changing Role of Forebrain Astrocytes During Development, Regenerative Failure, and Induced Regeneration upon Transplantation, 251 J. Comp. Neurol. 23–43 (1986).

The ability of cells to promote axonal outgrowth can be enhanced by expressing cell adhesion molecules, such as the L1 cell adhesion molecule on their surfaces, allowing even fibroblasts to promote neurite outgrowth following transplantation into the injured CNS. S. Kobayashi et al., Grafts of Genetically Modified Fibroblasts Expressing Neural Cell Adhesion Molecule L1 into Transected Spinal Cord of Adult Rats, 188 Neurosci-Lett. 191–94 (1995), hereby incorporated by reference. It is also known that expression by fibroblasts of neurotrophic factors can also enable these cells to promote neurite outgrowth in the CNS, e.g., R. Grill et al., Cellular Delivery of Neurotrophin-3 Promotes Corticospinal Axonal Growth and Partial Functional Recovery after Spinal Cord Injury, 17 J. Neurosci. 5560–72 (1997), and references therein; M. D. Kawaja et al., Grafting Genetically Modified Cells within the Rat Central Nervous System: Methodological Considerations, in Neural Transplantation: A Practical Approach 21–56 (S. B. Dunnett & A. Bjorklund eds., 1992), and references therein; L. F. Fisher et al., Use of Genetically Modified Cells to Deliver Neurotrophic Factors and Neurotransmitters to the Brain, in Providing Pharmacological Access to the Brain: Alternate Approaches 329–47 (R. Flanagan, D. F. Emerich, and S. R. Winn eds., 19__), and references therein, hereby incorporated by reference.

To enhance the ability of GRP cells and/or their derivatives to promote axonal outgrowth, the cells used for transplantation are first genetically transduced in vitro to stably express supranormal levels of one or more cell adhesion molecules known to promote neurite outgrowth (e.g., L1, Ng-CAM, CHL1, NCAM, and other comparable molecules well known to practitioners of the art). Any expression system known in the art can be used to express the therapeutic compound, so long as it has a promoter that is active in the cell, and appropriate internal signals for initiation, termination, and polyadenylation. Examples of suitable expression vectors include recombinant vaccinia virus vectors including pSC11, or vectors derived from viruses such as Simian Virus 40, Rous Sarcoma Virus, mouse mammary tumor virus, adenovirus, herpes simplex virus, bovine papillomavirus, Epstein-Barr virus, lentiviruses, or any other eukaryotic expression vector known in the art.

Genetically transduced GRP cells and/or their derivatives are implanted into the CNS as diffusible cells or on scaffolds, as described in Example 14, thus providing an exceptionally potent surface for the promotion of axonal growth in particular directions.

GRP cells and/or their derivatives growing on cellular scaffolds are implanted in such a manner as to form a bridge between a region where a desired population of neurons exists and the region(s) to which neuronal growth is being directed. For example, in the injured spinal cord, such scaffolds, on which genetically modified GRP cells and/or their derivatives are growing, are implanted such that a bridge is formed between the caudal and rostral portions of the injured spinal cord.

EXAMPLE 15
Use of GRP Cells and/or Their Derivatives for the Screening of Potentially Neurologically Therapeutic Compositions.

GRP cells or derivatives thereof or mixtures thereof cultured in vitro can be exposed to compositions of interest at varying dosages, and the response of the cells monitored for various time periods. The induction of expression of new or increased levels of proteins such as enzymes, receptors, and other cell surface molecules, or of neurotransmitters, amino acids, neuropeptides, and biogenic amines can be analyzed with any technique known in the art that can identify the alteration of the level of such molecules, including protein assays, enzymatic assays, receptor binding assays, enzyme-linked immuosorbent assays, electrophoretic analysis, analysis with high performance liquid chromatography, Western blots, and radioimmune assays. Nucleic acid analysis such as Northern hybridization can be used to examine the levels of mRNA coding for these molecules, or for the enzymes which synthesize these molecules. Cells can also be used to screen for compounds able to promote the division of GRP cells and/or their derivatives by determining the ability of compounds to cause increases in GRP cell number or to promote DNA synthesis, as measured by, e.g., incorporation of bromodeoxyuridine or tritiated thymidine. Cells can also be used to screen for compounds that promote survival of GRP cells and/or their derivatives by applying compounds to cells in conditions where they would be expected to die (e.g., exposure to neurotoxic agents, withdrawal of all trophic factors) and examining cell survival using any of the techniques well known to practitioners of the art. Cells can also be used to screen for compounds that specifically inhibit binding to particular receptors, by looking at the ability of said blocking compounds to block the response elicited by binding of agonist to said receptor. Cells can also be used to screen for compounds able to activate particular receptors using ligand binding assays well known to practitioners of the art, or by looking at such physiological alterations as are associated with activation of said receptor, such as fluxes in calcium levels, or other alterations well known to practitioners of the art.

Alternatively, cells treated with these pharmaceutical compositions can be transplanted into an animal and their survival, ability to form oligodendrocytes or astrocytes and to express any of the functions of these cell types can be analyzed by any procedures available in the art.

We claim:

1. A method of obtaining glial cells comprising:
    (a) isolating glial restricted precursor cells from central nervous system tissue by negative immunoselection of E-NCAM positive calls followed by positive immunoselection with an A2B5 antibody, said glial restricted precursor cells being immunonegative for PDGF-α receptor, PDGF-β receptor, and Ran-2 antigen, not labeled with R24 anti-GD3 antibody, and immnunopositive for A2B5 antigen; and
    (b) plating said isolated glial restricted precursor cells of step (a) under differentiating conditions, thereby causing said isolated glial restricted precursor cells to differentiate into glial cells.

2. The method of claim 1 wherein said differentiating conditions comprise addition to growth medium of an effective amount of fetal calf serum that promotes differentiation into non-process bearing A2B5$^-$GFAP$^+$ astrocytes so that said glial cells are A2B5$^-$GFAP$^+$ astrocytes.

3. The method of claim 1 wherein said differentiating conditions comprise addition to growth medium of an effective amount of ciliary growth factor and basic fibroblast growth factor that promotes differentiation into process bearing A2B5$^+$GFAP$^+$ astrocytes so that said glial cells are A2B5$^+$GFAP$^+$ astrocytes.

4. The method of claim 1 wherein said differentiating conditions comprise addition to growth medium of an effective amount of platelet-derived growth factor and thyroid hormone (T3) that promotes differentiation into oligodendrocytes so that said glial cells are oligodendrocytes.

5. A method for continuously propagating glial restricted precursor cells immunonegative for PDGF-α receptor, PDGF-β receptor, and Ran-2 antigen, not labeled with R24 anti-GD3 antibody, and immunopositive for A2B5 antigen comprising the steps of:
    (a) isolating glial restricted precursor cells from central nervous system tissue by negative immunoselection of E-NCAM positive cells followed by positive immunoselection with an A2B5 antibody, said glial restricted precursor cells being immunonegative for PDGF-α receptor, PDGF-β receptor, and Ran-2 antigen, not labeled with R24 anti-GD3 antibody, and immunopositive for A2B5 antigen; and
    (b) culturing said isolated glial restricted precursor cells of step (a) in vitro in the presence of minimal essential salts and effective amounts of platelet derived growth factor and fibroblast growth factor.

* * * * *

UNITED STATES PATENT AND TRADEMARK OFFICE
CERTIFICATE OF CORRECTION

PATENT NO. : 6,900,054 B2
APPLICATION NO. : 09/736728
DATED : May 31, 2005
INVENTOR(S) : Rao et al.

It is certified that error appears in the above-identified patent and that said Letters Patent is hereby corrected as shown below:

At column 1, line 8 immediately preceding the BACKGROUND OF THE INVENTION, please insert:

--This invention was made with government support under Grant #R29 NS035087 awarded by the National Institutes of Health. The Government has certain rights to this invention--.

Signed and Sealed this

Twenty-third Day of June, 2009

JOHN DOLL
*Acting Director of the United States Patent and Trademark Office*